US007275275B2

(12) United States Patent
Pankow et al.

(10) Patent No.: US 7,275,275 B2
(45) Date of Patent: Oct. 2, 2007

(54) CONTACT LENS TREATMENT APPARATUS

(75) Inventors: Mark L. Pankow, Chicago, IL (US); Charles C. Valauskas, Chicago, IL (US)

(73) Assignee: Iso Clear, Inc., Chicago, IL (US)

( * ) Notice: Subject to any disclaimer, the term of this patent is extended or adjusted under 35 U.S.C. 154(b) by 285 days.

(21) Appl. No.: 10/470,170

(22) PCT Filed: Jan. 26, 2001

(86) PCT No.: PCT/US01/02532

§ 371 (c)(1),
(2), (4) Date: Feb. 12, 2004

(87) PCT Pub. No.: WO01/55779

PCT Pub. Date: Aug. 2, 2001

(65) Prior Publication Data

US 2004/0134005 A1    Jul. 15, 2004

(51) Int. Cl.
*G02C 13/00*    (2006.01)
*B08B 11/00*    (2006.01)

(52) U.S. Cl. .............................. 15/104.92; 15/104.93; 15/214; 15/244.1; 206/5.1

(58) Field of Classification Search ............. 15/104.92, 15/104.93, 209.1, 214, 210.1, 244.1, 244.3, 15/208; 206/5.1; 134/901
See application file for complete search history.

(56) References Cited

U.S. PATENT DOCUMENTS

| 4,187,574 | A | * | 2/1980 | Wrue | 15/104.92 |
|---|---|---|---|---|---|
| 5,439,572 | A | * | 8/1995 | Pankow | 204/450 |
| 5,494,528 | A | * | 2/1996 | Beckrich | 134/6 |
| 5,657,506 | A | * | 8/1997 | Pankow | 15/104.92 |
| 6,138,312 | A | * | 10/2000 | Cummings | 15/104.92 |

* cited by examiner

*Primary Examiner*—Gary K. Graham
(74) *Attorney, Agent, or Firm*—Cook, Alex, McFarron, Manzo, Cummings & Mehler, Ltd.

(57) ABSTRACT

An apparatus (100) for cleaning contact lenses is disclosed. The apparatus comprises a housing (110) having first (112) and second (114) housing sections which are joinable to form a chamber for receiving the lens. Each of the housing sections has an operative face (118, 120, 124, 126) facing the chamber formed for receiving the lens. A reactive layer (122) is provided on a portion of each operative face and the operative faces and the reactive layers are dimensioned and arranged whereby the reactive layers come into engagement with respective surfaces of a lens (155) positioned therebetween when the first and second housing sections are joined together. A portion of at least one of the operative faces is recessed relative to the other operative face to define an open volume within the chamber when the first and second housing sections are joined together. The first and second housing sections can be constructed to be in fluid communication when the apparatus is in an opened position.

2 Claims, 4 Drawing Sheets

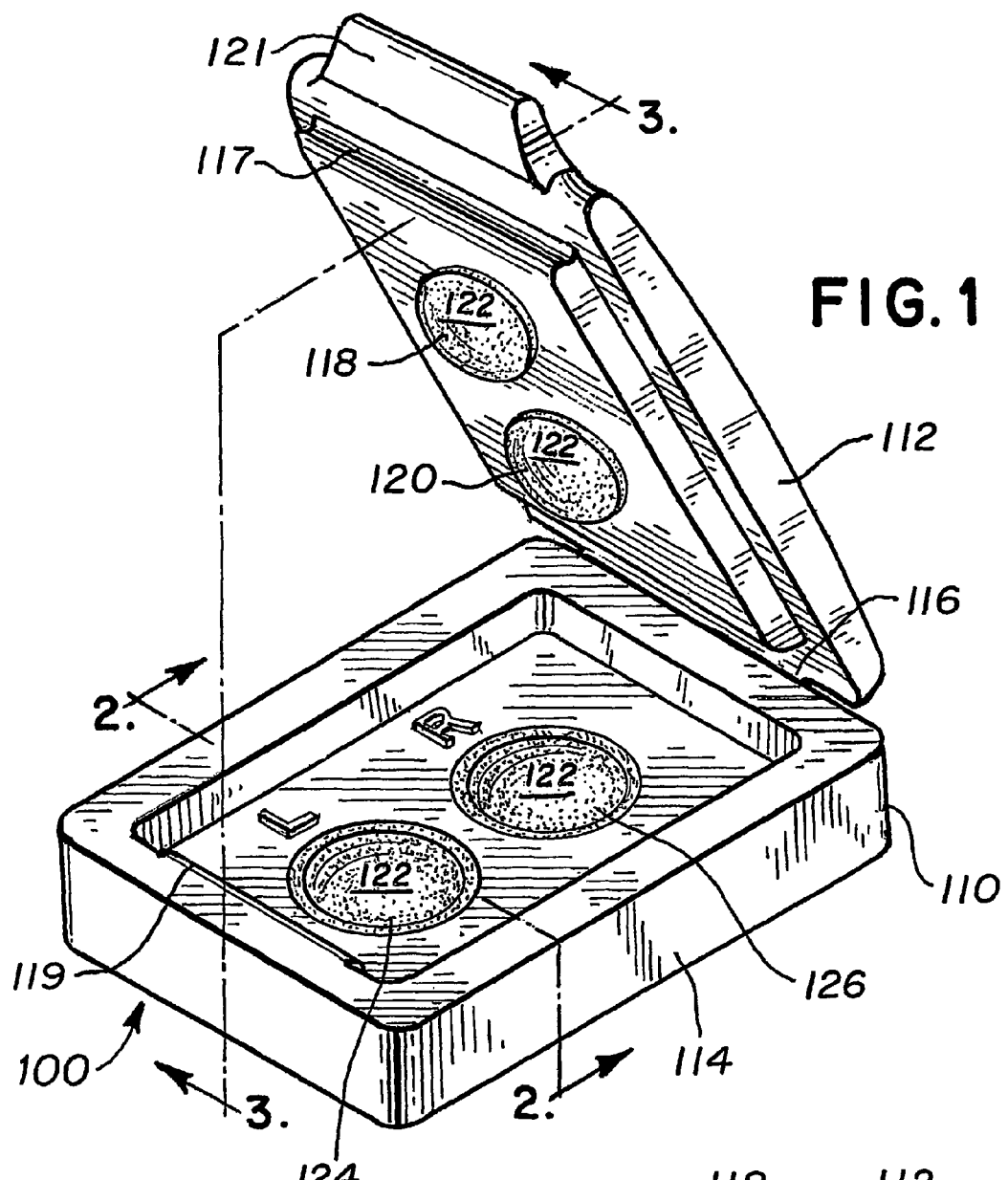
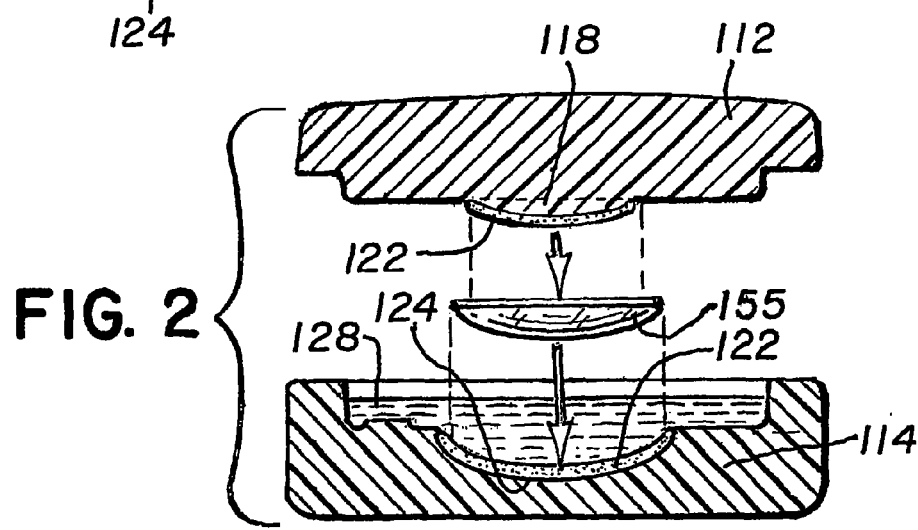

CONTACT LENS TREATMENT APPARATUS

BACKGROUND OF THE INVENTION

The present invention is directed to an apparatus and method for treating contact lenses. More particularly, the invention is directed to a stand-alone apparatus and method for using same by which contact lenses can be cleaned. In a particularly advantageous form, the apparatus is single-use and disposable, and comprises a housing including a pair of closable liquid sealed containers sized and shaped to accept and retain a lens therein such that the lens is brought into contiguous wetted contact with a reactive layer during the treatment process.

Contact lenses have come into wide use for correcting a wide range of vision deficiencies or cosmetic use. Typically, such lenses are formed from a thin transparent plastic material shaped and dimensioned to fit over the cornea of the eye. The lenses have an optical surface that includes a concave interior first optical surface for contact with the eye, an opposed and optically associated convex exterior second optical surface, and a surrounding edge. The two surfaces together define a corrective lens medically prescribed for a particular eye.

Depending on the polymer material used to construct the lenses, the lenses may be either "hard" or "soft". Hard contact lenses, which are comparatively more rigid, are typically formed from a relatively hydrophobic material such as polymethyl methacrylate (PMMA). Soft contact lenses, which are comparatively more pliant, are typically formed from a relatively hydrophilic polymer such as hydroxyethylmethacrylate (HEMA), which has the property of being able to absorb and bind a proportionately large amount of water within the polymer network. Soft contact lenses formed from such hydrophilic polymers, when hydrated, are more comfortable to wear than hard lenses because they conform better to the cornea of the eye and cause less irritation when worn for extended periods. For this reason, the great majority of contact lenses presently being prescribed are of the soft type.

Unfortunately, soft contact lenses while being worn may collect contaminants from the eye and its environment. These contaminants, for example, may include proteins and lipids, including denatured ones, from the tear fluid of the eye, and foreign substances such as cosmetics, soaps, air-borne chemicals, dust and other particulate matter. Unless periodically removed, these contaminants may cause abrasion to the surface of the eye, may impair the visual acuity of the lens, and may serve as a nutrient media for potentially harmful microorganisms.

Furthermore, for wearing comfort it is necessary that soft contact lenses be maintained uniformly wetted at all times. While on the eye, the moisture content of the hydrophilic material of the lenses is maintained by tear fluid. However, when the lenses are removed for an extended period, as for cleaning or while sleeping, the lenses may dry out and become irreversibly damaged unless they are externally hydrated.

Consequently, various apparatus and methods have been developed for cleaning and hydrating soft contact lenses. For example, cleaning apparatus has been provided wherein the lenses are submersed in a variety of liquid cleaning agents, such as surfactants, oxidants, disinfectants, enzymatic cleaners, or abrasives. Other cleaning apparatus has been provided which included mechanically operated or electrically powered components for vibrating, rotating, abrading, scrubbing, heating, agitating, subjecting to ultra-sonic energy, or otherwise mechanically manipulating the lenses to enhance the cleaning action of the cleaning agent.

Such prior apparatus and methods have not been entirely satisfactory for various reasons, including lack of cleaning effectiveness with respect to certain of the various contaminants found on the lenses, undesirable complexity, excessive time required for use, harshness to the lens material, and dependence on an external power source.

One apparatus which overcomes these shortcomings is described in U.S. Pat. No. 5,657,506, the disclosure of which is incorporated by reference herein. The apparatus utilizes a two-piece lens container wherein the exposed surfaces of two sponge members, wetted with an opthalmologically compatible solution, and each having thereon a reactive layer formed of a highly porous non-abrasive relatively polymeric material such as polytetrafluoroethylene (PTFE), are brought into compressive engagement with the optical surfaces of an interposed contact lens whereby the reactive layers cause contaminants to migrate from the lens to the reactive layers. Alternate apparatus are also disclosed in U.S. Pat. No. 6,138,312, the disclosure of which is incorporated by reference herein.

The present invention is directed to alternate constructions from those described in U.S. Pat. Nos. 5,657,506 and 6,138,312.

Accordingly, it is a general object of the present invention to provide a new and improved apparatus for cleaning contaminated contact lenses.

It is a more specific object of the invention to provide an apparatus for cleaning contaminated contact lenses which is simple to use and economical to manufacture.

It is a further object of the present invention to provide a disposable single-use apparatus for cleaning contaminated contact lenses having closable liquid-sealed container within which the lenses are contained while being cleaned.

It is a further object of the invention to provide a self contained apparatus for cleaning a contaminated contact lenses wherein the optical surfaces of the lenses may be received in a wetted environment in contiguous contact with a reactive medium whereby lenses can be generally cleaned without the application of abrasive force (e.g. without the force caused when rubbing the lens by hand).

SUMMARY OF THE INVENTION

The invention is directed to an apparatus for cleaning contact lenses of the type having a pair of opposed optical surfaces, comprising a non-abrasive reactive surface operative when in contact with the optical surface of the lens to reduce contaminant matter on the lens, the reactive surface being wetable and shaped for generally contiguous engagement between the optical surface and the reactive surface. In one embodiment the apparatus comprises a housing having first and second housing sections which are joinable to form a chamber for receiving the lens. Each of the housing sections has an operative face facing the chamber formed for receiving the lens. A reactive layer is provided on a portion of each operative face and the operative faces and the reactive layers are dimensioned and arranged whereby the reactive layers come into engagement with respective optical surfaces of a lens positioned therebetween when the first and second housing sections are joined together. A portion of at least one of the operative faces is recessed relative to the other operative face to define an open volume within the chamber when the first and second housing sections are joined together. The open volume is capable of retaining an ophthalmologically compatible solution within the apparatus thereby providing a location for excess fluid to well without leaking from the apparatus. Preferably the operative faces are comprised of a compliant material and more preferably they are comprised of a compliant and absorbent material. The compliant material can take a variety of forms and, for example, can be made from fibrous cellulose material, a sponge material and/or a thin film such as a metal foil material to name a few. The first and second housing sections can be constructed to be in fluid communication when the apparatus is in an opened position to, for example, encourage drainage of fluid from one section to the other section. The apparatus can be constructed to be deformable, in whole or part, to provide a reduced volume inside the apparatus. These and other features of the invention are described in detail below.

BRIEF DESCRIPTION OF THE DRAWINGS

The invention, together with the further objects and advantages thereof, may best be understood by reference to the following description taken in conjunction with the accompanying drawings, in the several figures of which like reference numerals identify like elements, and in which:

FIG. 1 is a perspective view of one embodiment of a lens cleaning apparatus in accordance with the present invention in a partially closed position.

FIG. 2 is an exploded cross-sectional view of the lens cleaning apparatus of FIG. 1 in a folded over (closed) position taken along line 2—2 of FIG. 1

DESCRIPTION OF THE PREFERRED EMBODIMENT

Figure 3:
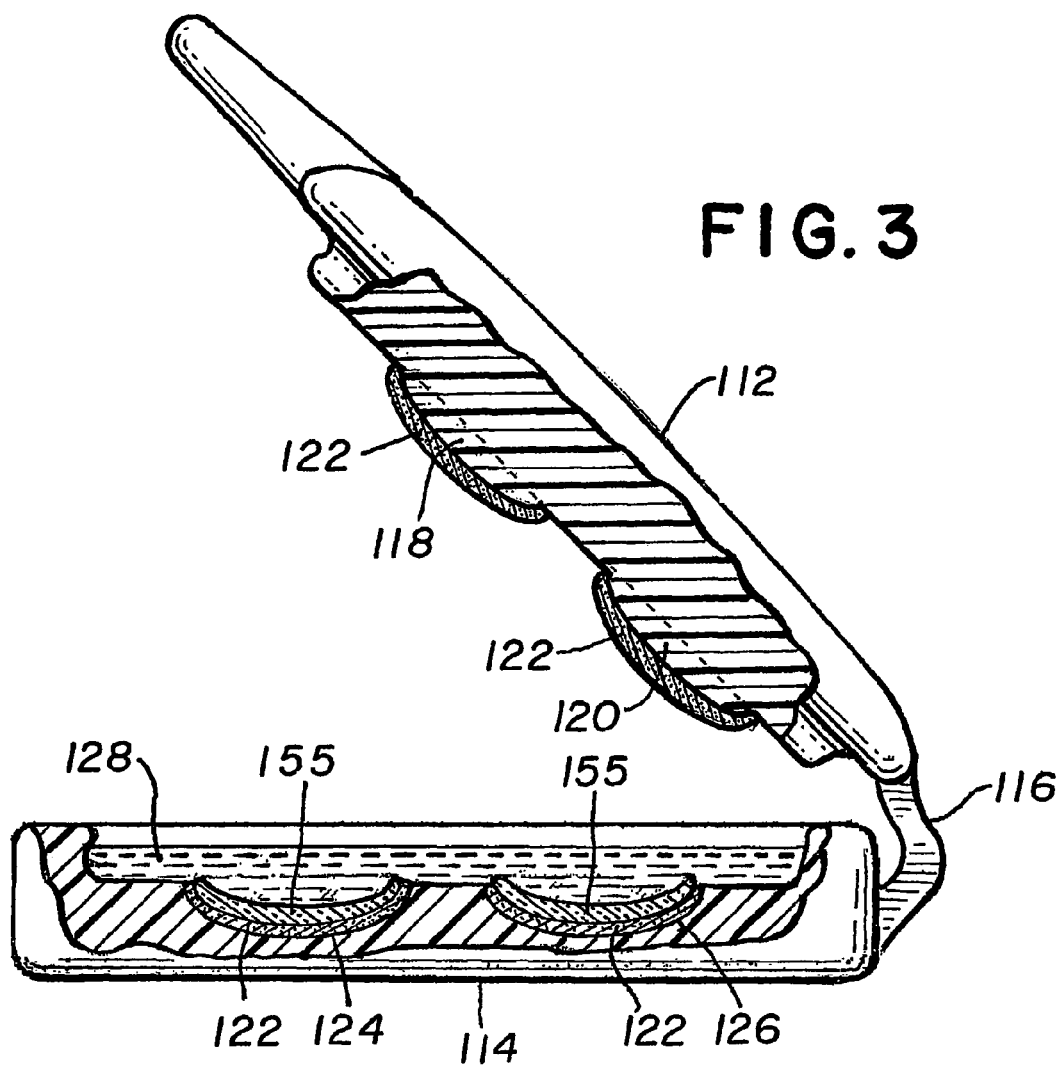
FIG. 3 is a cross-sectional view of the lens cleaning apparatus of FIG. 1 taken along line 3–3 of FIG. 1.

Referring to the figures, FIGS. 1–4, show an embodiment of a lens treatment apparatus 100 in accordance with the invention and is seen to include a container 110 having an upper body section 112 and a lower body section 114. Preferably the upper and lower body sections are joined together by hinged portion or fold line 116 which can take any suitable form. For example, hinge or fold line 116 can be a living hinge. The interior of the upper body section 112 includes convex surface portions 118 and 120. A layer of reactive material 122 covers convex portions 118 and 120. The interior of lower body section 114 includes concave surface portions 124 and 126. A layer of reactive material 122 covers concave portions 124 and 126.

Convex portions 118 and 120 and concave portions 124 and 126 are generally dimensioned and positioned to cooperatively engage contact lenses 155 placed in the container 110 when the container is closed. Preferably, the interior of lower body section 114 includes a recessed portion 128 surrounding the concave portions 124 and 126 for holding an opthalmological compatible solution which solution can be prepackaged with the apparatus or placed in the apparatus prior to use. When contact lenses are placed in the apparatus for cleaning and the apparatus is closed, solution flows around the reactive layers 122 providing a fluid interface between the optical surface of the lens and the contacting surfaces of reactive layers 122, respectively.

The container body 110 can be constructed from any suitable material and can be constructed for single use or repeated use applications. For example container body 110 can be constructed from polymeric materials, including synthetic polymers such as polyethylene, polypropylene, polyvinyl chloride, polyethylene terephthalate and other similar materials and can include common additives including, but not limited to, fillers, pigments and plasticizers. Container body 110 can also be constructed from natural materials such as cellulose. For example, a preferred material for container body 110 is a fibrous cellulose which is compliant and absorbent.

When using an absorbent material such as fibrous cellulose for container body 110 it may be desirable to treat or coat the exterior of container body 110 to provide the container with a moisture impermeable barrier to prevent leakage of the solution from the container. For example, a wax can be applied to the exterior of an absorbent container body such as a cellulose container body to provide a moisture barrier. Alternatively, a plastic coating or metal foil can be applied to the exterior of such a container body to provide a moisture barrier. Alternatively, container body 110 can be constructed from a moisture impermeable shell such as a shell made from a synthetic polymer and an absorbent cellulose insert dimensioned to fit within such shell.

Convex portions 118 and 120 and concave portions 124 and 126 can be formed directly in container body 110 or can be in the form of inserts for container body 110. The reactive layers 122 also can be supplied in a variety of ways. For example, convex portions 118 and 120 and concave portions 124 and 126 can be made from an absorbent cellulose material and reactive layer 122 can be provided directly to the surface of such portions, 118, 120, 124 and 126. Reactive layer 122 can be constructed from a variety of reactive matter including matter having a higher physical or chemical affinity for the contaminants relative to the material of the lens, and from matter having active sites such as enzymatic sites for cleaning and thereby facilitating removal of contaminants from the lens.

Alternatively, reactive layer 122 can take the form of a separate sheet or film such as a sheet or a film of PTFE or of a solid phase having enzymatic matter bound to it such as a cellulose paper which is coated with enzymatic matter. The cellulose paper can be in sheet form which is pre-applied to the external surfaces of the interior of container body 110 or in sheet form which is supplied separately for insertion into container body 110. It will be appreciated that such sheet form can be provided in different sizes and configurations to enable ease of use and accommodate economy concerns.

For example, reactive layer sheets 122 can be sized to fit within the container body 110 and entirely coated with reactive matter to guard against misalignment of the sheets when inserted into the container body relative to the location of convex and concave portions 118, 120, 124, and 126. Alternatively, the sheets can be sized to fit within the container body and the coating of reactive matter can be limited to those areas of the sheet designed to align with convex and concave portions 118, 120, 124, and 126. Alternatively, reactive layer 122 can be a solid phase having bound reactive matter, such as an enzyme coated cellulose paper, in "button" form which is sized and dimensioned for direct placement on convex and concave portions 118, 120, 124, and 126.

Figure 4:
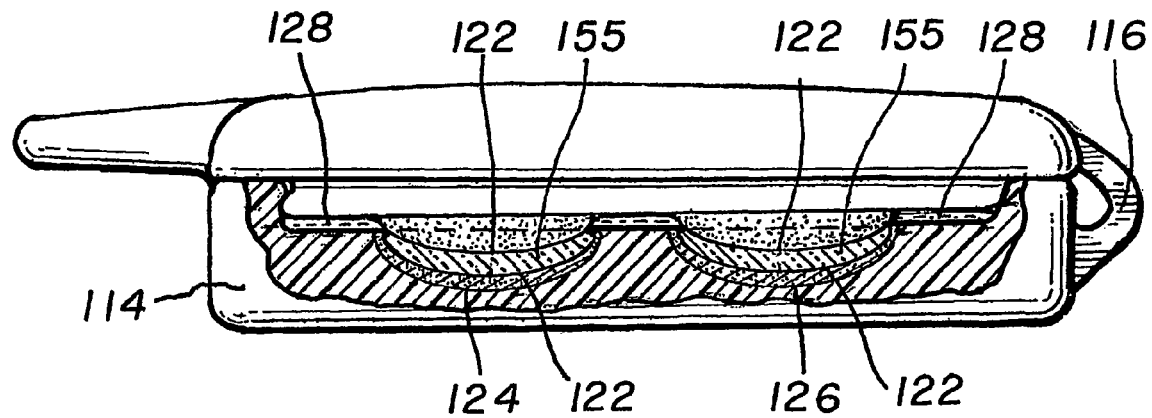
FIG. 4 is a cross sectional view of the lens cleaning apparatus of FIG. 1 in a closed position.

During use, the user places the contact lens to be cleaned on reactive layer of the first body section. The second body section is then folded over the first body section. As shown in FIG. 4, when the apparatus is closed the reactive surfaces of the first and second body sections are brought into contiguous engagement of the optical surfaces of a lens. The second body section and the first body section are held together the closed arrangement through a releaseable latch and when latched together the first and second body sections preferably form a fluid tight housing. For example, lower body section 114 can be formed to include a ledge 119 which engages a complimentary shaped resilient protrusion 117 formed in upper body section 112 to maintain lower body section 114 and upper body section 112 in a liquid sealed condition for containing liquid within the container. One or both of lower body section 114 and upper body section 112 can include a tab 121 to facilitate opening and closing the container. As shown in FIG. 4, when the first and second body sections are brought together there is a conforming contiguous contact between the optical surfaces of lens and the respective contacting reactive layer surfaces and there is a defined volume inside the chamber capable of holding excess ophthalmological fluid.

Figure 6:
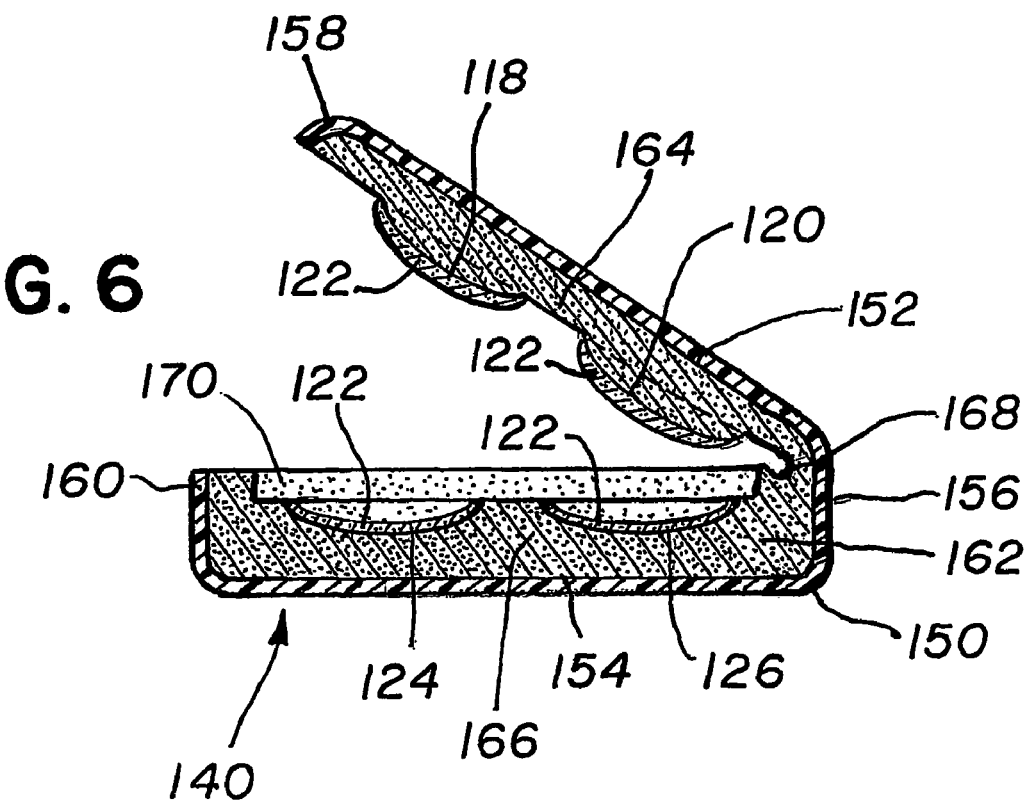
FIG. 6 is a cross sectional view of another embodiment of a lens cleaning apparatus in accordance with the present invention.

FIG. 6 shows another embodiment of a lens treatment apparatus 140 in accordance with the present invention including a container 150 having an upper body section 152 and a lower body section 154 flexibly joined together by spine 156. Upper body section 152 and lower body section 154 are recessed forming chambers 158, 160 respectively, with lower chamber 160 having a greater depth than upper chamber 158. A sponge material 162 dimensioned to fit snugly in chambers 158 and 160 is positioned in container 150.

The sponge material 162 has an upper body portion 164 and a lower body portion 166 joined together by spine portion 168 so that upper body portion 164 and lower body portion 166 are in fluid communication through spine portion 168.

The sponge material is provided with generally convex surfaces 118 and 120 and generally concave surfaces 124 and 126 over which is a thin layer of reactive material 122. Prior to use of the apparatus 140, sponge material 162 is preferably moistened with an opthalmologically compatible solution. The solution can be prepackaged with the apparatus or placed in the apparatus prior to use.

The apparatus is opened to receive contact lenses for cleaning. When contact lenses are inserted in the apparatus for cleaning, the apparatus is closed by the user and the accompanying compression of sponge sections 164 and 166 causes solution absorbed therein to flow around the ends of reactive layers 122 and around and under the lenses providing a fluid communication interface.

Preferably lower section 160 has a recessed section to form a well or internal collection chamber 170 for the opthalmologically compatible solution to retain excess fluid and to mitigate against fluid seeping out of the apparatus. After use the apparatus is opened and the lenses are removed. When left open, fluid retained in upper sponge body portion 164 is drawn to lower sponge 166 through sponge spine portion 168 due to the difference in the relative fluid retaining capacities of upper sponge body portion 164 and lower sponge body portion 166 and gravity. In particular, because of the depth of recess forming chamber 158 relative to the depth of chamber 160, lower portion 166 has a greater fluid retaining capacity than upper section 164 due to its greater volume.

Figure 5:
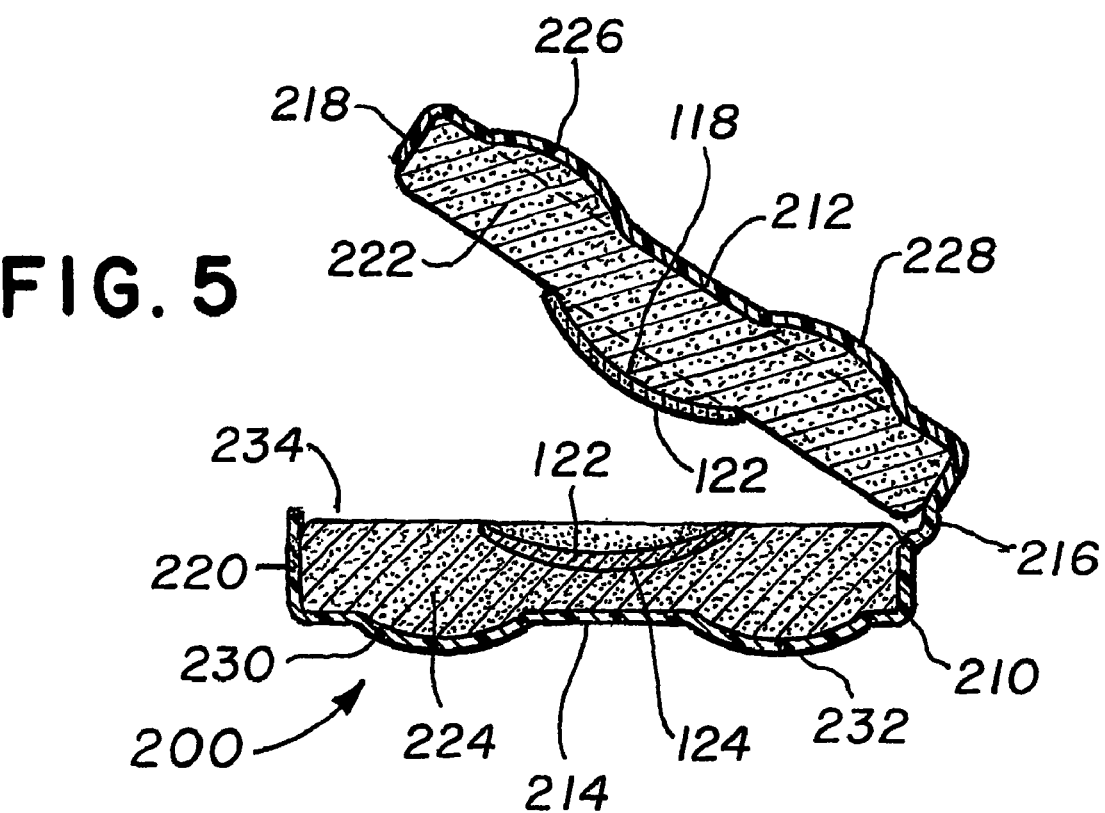
FIG. 5 is a cross sectional view of another embodiment of a lens cleaning apparatus in accordance with the present invention.

FIG. 5 shows another embodiment of a lens treatment apparatus 200 constructed in accordance with the present invention including a container 210 having an upper body section 212 and a lower body section 214 flexibly joined together by spine 216. Upper body section 212 and lower body section 214 are recessed forming chambers 218, 220, respectively. A sponge material 222 dimensioned to fit snugly in chamber 218 is positioned in container 210. A sponge material 224 dimensioned to fit snugly in chamber 220 is positioned in container 210. Upper sponge 222 is dimensioned to have a greater depth than the depth of upper section 218, that is sponge 22 is oversized relative to the depth of section 218, and sponge section 224 is dimensioned to have a depth less than that of lower section 220, that is it is undersized relative to the depth of section 220. Sponge 222 and 224 are dimensioned so that their respective depths are complementary so that when apparatus 200 is in a closed configuration sponge 222 and sponge 224 are in a relatively compressive configuration with respect to each other. Sponge 222 is provided with a cooperatively aligned, generally convex surface 118 and sponge section 224 is provided with generally concave surface 124 over each of which is a thin layer of reactive material 122. Upper section 218 is provided with inwardly deformable portions 226, 228 and lower section 220 is preferably also provided with inwardly deformable portions 230, 232.

Prior to use of the apparatus 200, sponge 222 and 224 are preferably moistened with an opthalmologically compatible solution. The solution can be prepackaged with the apparatus or placed in the apparatus prior to use. The apparatus is opened to receive contact lenses for cleaning. After the contact lenses are inserted in the apparatus for cleaning, the apparatus is closed by the user. The user then depresses inwardly deformable portions 226, 228, 230 and 232 and the depression of those sections together with the compression of sponge 222 and 224 causes solution absorbed in sponges 222 and 224 to flow around the ends of reactive layers 122 and around and under the lenses providing a fluid communication interface. Preferably inwardly deformable portions 226, 228, 230, and 232 are generally irreversibly deformable to promote disposal of the unit after use. The differential in height between lower section 220 and lower sponge 224 forms a well or internal collection chamber 234 for the optimologically compatible solution to retain excess fluid and to mitigate against fluid seeping out of the apparatus during use or when the apparatus is opened. While apparatus 200 has been shown to include a single convex portion 118 and a single concave portion 124, it will be appreciated by those skilled in the art that a plurality of concave and convex portions can be provided so that apparatus 200 can be used to clean more than one lens at one time.

Figure 7:
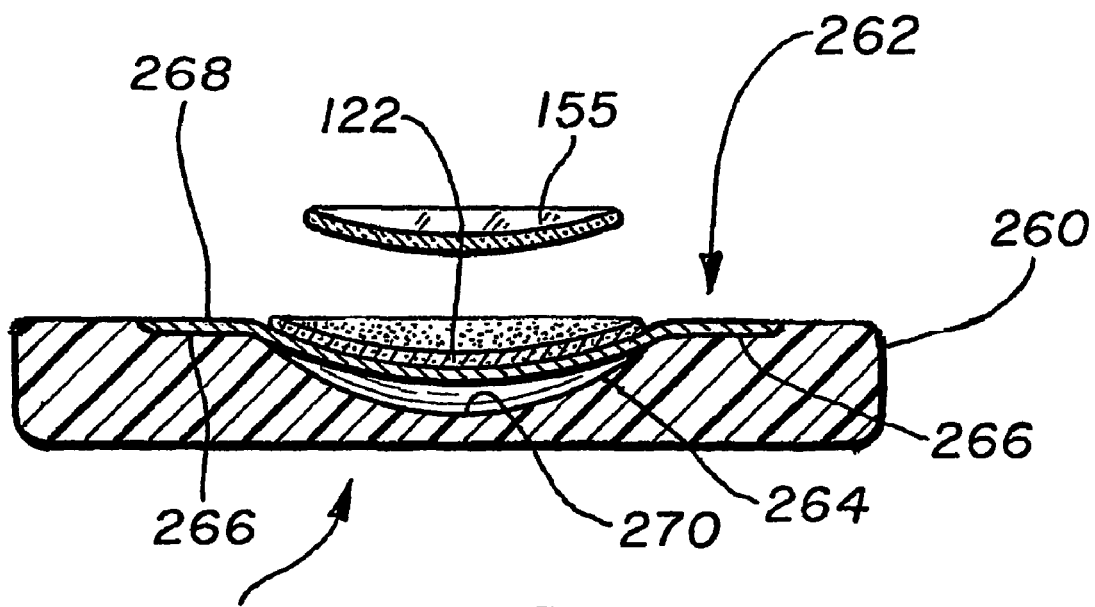
FIG. 7 is a cross-sectional view of the lower half of another embodiment of a lens cleaning apparatus in accordance with the present invention.

FIG. 7 shows the lower half of another embodiment of a lens treatment apparatus 250 in accordance with the present invention including a container 260 having cooperative upper body and lower body sections joined together by a hinged portion or fold line similar to the construction shown for apparatus 100 in FIG. 1. While the following discussion of FIG. 7 is directed to the configuration of the lower body section of apparatus 250, it will be appreciated by those skilled in the art that the upper body section will be constructed in a complementary manner to cooperatively provide a working lens treatment apparatus. With specific reference to FIG. 7, apparatus 250 is seen to have a lower body section 260 having an interior portion 262. The interior portion 262 of lower body section 260 is formed to have a concave recessed portion 264 surrounded by shoulders 266. A relatively thin layer or film of compliant material 268, such as a deformable metal foil is adhered to and supported by shoulders 266. Compliant layer 268 spans recess 264, and partially or fully covers recess 264. A layer of reactive material 122 covers the recess covering portion of compliant layer 268. A pocket 270, filled with air or other highly compliant matter, is formed between compliant layer 268 and recess 264 which provides a compliant cushion for a lens placed into apparatus 260 for cleaning.

Figure 8:
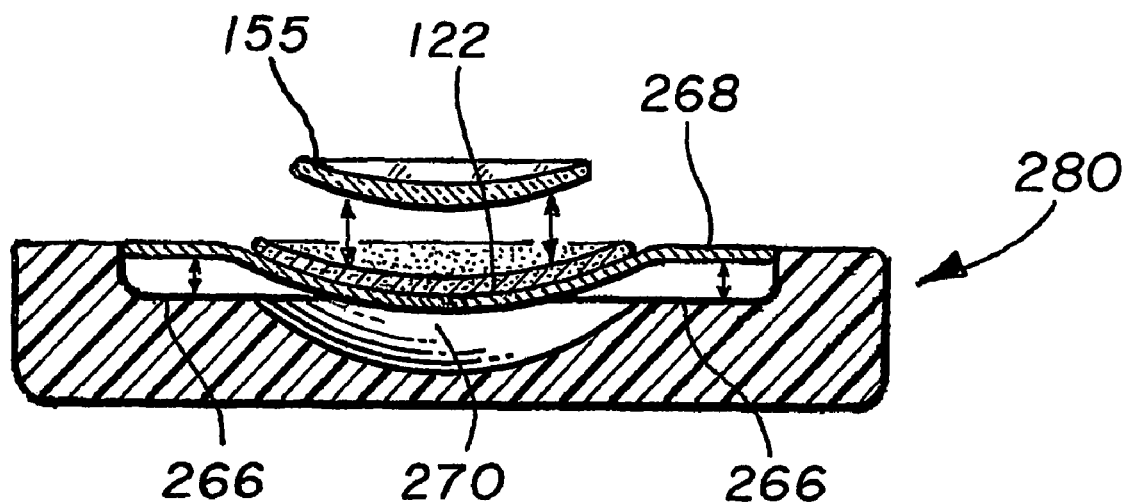
FIG. 8 is a cross-sectional view of the lower half of another embodiment of a lens cleaning apparatus in accordance with the present invention.

FIG. 8 shows the lower half of another embodiment of a lens treatment apparatus 280 in accordance with the present invention. The embodiment shown in FIG. 8 is similar to the embodiment shown in FIG. 7. The embodiment shown in FIG. 8 differs from that shown in FIG. 7 in that the compliant layer 268 is supported above, instead of on, shoulders 266 to ensure the lens is cushioned regardless of its location on complaint layer 268. In the embodiments illustrated in FIG. 7 and FIG. 8, pocket 270 also defines an interior volume within the chamber which can also hold an opthalmologically compatible solution to provide a moist environment for reactive layer 122 and/or lens 155.

While particular embodiments of the invention have been shown and described, it will be obvious to those skilled in the art that changes and modifications may be made thereto without departing from the invention in its broader respects. In that regard, it will, of course, be appreciated that the features of the various embodiments can be interchanged and combined to form lens cleaning apparatus within the scope of the present invention. For example, the lens cleaning apparatus could be constructed with one section having a sponge member supporting the reactive layer and the other section having a different compliant material supporting its associated reactive layer, e.g. fibrous cellulose or a thin film such as a compliant metal foil. Additionally, it will be appreciated that the deformable case features illustrated and described with reference to FIG. 5 can be incorporated in other embodiments of the invention including, but not limited to, those shown in FIGS. 1–4 and 6 herein. Additionally, the lens cleaning apparatus of the present invention can be constructed to receive a single lens or a plurality of lenses. Accordingly, the aim in the appended claims is to cover all such changes and modifications as fall within the true spirit and scope of the invention.

We claim:

1. A contact lens cleaning apparatus for cleaning contact lenses of the type having generally opposed optical surface, comprising: a generally rigid base member having a first portion and a second portion; a first recess forming a first chamber on a top surface of said first base portion, said first chamber having an open end and closed end; a second recess forming a second chamber on said top surface of said first base portion, said second chamber having an open end and a closed end; said first and second portions being joinable so that said second base portion can be positioned on said first base portion with said open ends of said chambers in general alignment; a first compliant material comprising a deformable metal foil disposed in said first chamber, at least a portion of said first compliant material spaced apart from said closed end of said first chamber and having an operative face facing said open end of said first chamber; a second compliant material disposed in said second chamber, at least a portion of said second compliant material spaced apart from said closed end of said second chamber and having an operative face facing said open end of said second chamber; a portion of said operative faces each including a reactive layer; said operative faces coming into compliant engagement when said first and second portions are joined together whereby said reactive layers come into engagement with respective optical surfacing of a lens positioned therebetween.

2. A contact lens cleaning apparatus as defined in claim 1 wherein a portion of said first compliant material is supported by a portion of said closed end of said first chamber and a portion of said second compliant material is supported by a portion of said closed end of said second chamber.

* * * * *